United States Patent [19]

Wu

[11] Patent Number: 5,358,852
[45] Date of Patent: Oct. 25, 1994

[54] USE OF CALCIUM IN IMMUNOASSAY FOR MEASUREMENT OF C-REACTIVE PROTEIN

[75] Inventor: Annie L. Wu, Penfield, N.Y.

[73] Assignee: Eastman Kodak Company, Rochester, N.Y.

[21] Appl. No.: 993,569

[22] Filed: Dec. 21, 1992

[51] Int. Cl.$^5$ ................ G01N 33/531; G01N 33/543; G01N 30/91

[52] U.S. Cl. .................................. 435/7.94; 435/7.9; 435/7.92; 436/518; 422/56; 422/68.1

[58] Field of Search ................... 422/68.1, 56; 435/7.9, 435/7.92, 7.94, 970; 436/518, 528, 531, 532, 815

[56] References Cited

U.S. PATENT DOCUMENTS

| | | | |
|---|---|---|---|
| 3,992,158 | 11/1976 | Przybylowicz et al. | 422/57 |
| 4,751,190 | 6/1988 | Chiapetta et al. | 436/546 |
| 4,780,422 | 10/1988 | Mitani et al. | 436/524 |
| 4,781,890 | 11/1988 | Arai et al. | 422/56 |
| 4,782,014 | 11/1988 | Serban et al. | 435/7 |
| 4,839,276 | 6/1989 | Adolfsen et al. | 435/7 |
| 4,902,630 | 2/1990 | Bennett et al. | 436/546 |
| 4,913,883 | 4/1990 | Imai et al. | 422/82.01 |
| 5,003,065 | 3/1991 | Merritt et al. | 540/469 |
| 5,128,270 | 7/1992 | Delacroix et al. | 436/518 |

FOREIGN PATENT DOCUMENTS

| | | |
|---|---|---|
| 0101945 | 8/1986 | European Pat. Off. |
| 0468585 | 1/1992 | European Pat. Off. |
| 2217335 | 10/1989 | United Kingdom . |

OTHER PUBLICATIONS

Coll "Development of a Fast Solid-Phase Enzyme Immunoassay For C-Reactive Protein" Rev. esp. Fisiol., 44(4) 359-368, 1988.

Catty *Antibodies: A Practical Approach* vol. 1, IRL Press, Oxford England (1988) p. 14.

"Specificity of C-Reactive Protein for Choline Phosphate Residues of Pheumococcal C-Polysaccharide (35323)" by John E. Volanakis and Melvin H. Kaplan; Department of Medicine, Case Western Reserve University School of Medicine and Metropolitan General Hospital, Cleveland, Ohio 44109; pp. 612-614.

"Comparison of the Secondary Structures and Binding Sites of C-Reactive Protein and the Phosphorylcholine-Binding Muring Myeloma Proteins[1]" by N. Martin Young and Ross E. Williams; *The Journal of Immunology*, Copyright 1978 by The Williams & Wilkins Co.; vol. 121, No. 5, Nov. 1978; pp. 1893-1898.

"Demonstration of Calcium-Induced Conformational Chenge(s) in C-Reactive Protein by Using Monoclonal Antibodies" by J. Michael Kilpatrick, John F. Kearney and John E. Volanakis; *Molecular Immunology*, Copyright 1982 by Pergamon Press Ltd.; vol. 19, No. 9; pp. 1159-1165.

(List continued on next page.)

*Primary Examiner*—Toni R. Scheiner
*Assistant Examiner*—Lora M. Green
*Attorney, Agent, or Firm*—John R. Everett

[57] ABSTRACT

A specific binding immunoassay method for reducing the "hook" effect for the measurement of C-Reactive Protein has been discovered for both solution and dry analytical elements comprising contacting a liquid sample containing C-reactive protein in the presence of calcium ions with (a) a first antibody Ab1 specific for C-reactive protein, Ab1 being immobilized on a water-insoluble substrate and (b) a labeled, unbound second antibody Ab2 specific for C-reactive protein to obtain a water-insoluble complex of Ab1, ligand, and Ab2; (2) separating the water-insoluble complex from the liquid sample and unreacted Ab2; and (3) measuring either the amount of Ab2 associated with said water-insoluble complex or the amount of unreacted Ab2 as an indication of the amount of C-reactive protein in the sample.

8 Claims, 1 Drawing Sheet

OTHER PUBLICATIONS

"Monoclonal Antibodies to the Calcium-Binding Region Peptide of Human C-Reactive Protein Alter its Conformation" by Steven J. Swanson, Michael C. Mullenix and Richard F. Mortensen; *The Journal of Immunology*, Copyright 1991 by The American Association of Immunologists; vol. 147, No. 7, Oct. 1, 1991; pp. 2248–2252.

"Identification and Partial Characterization of Multiple Native and Neoantigenic Epitopes of Human C-Reactive Protein by Using Monoclonal Antibodies[1]" by Shan-Ching Ying, Henry Gewurz, Carol M. Kinoshita, Lawrence A. Potempa and Joan N. Siegel; *The Journal of Immunology*, Copyright 1989 by the American Association of Immunologists; vol. 143, No. 1, Jul. 1, 1989; pp. 221–228.

J58171-668-A, "High Sensitivity Multilayer Analytical Element"; Konishiroku Photo KK; *Chem. Abst.* C83-111610.

J52123-295, "Reagent for Determination of Carbon-Reactive Protein"; Eiken Kagaku KK; *Chem. Abst.*

J0 1171-567-A, "Calcium Phosphate Immuno-Adsorbent for Blood"; Advance KK; *Chem. Abst.*

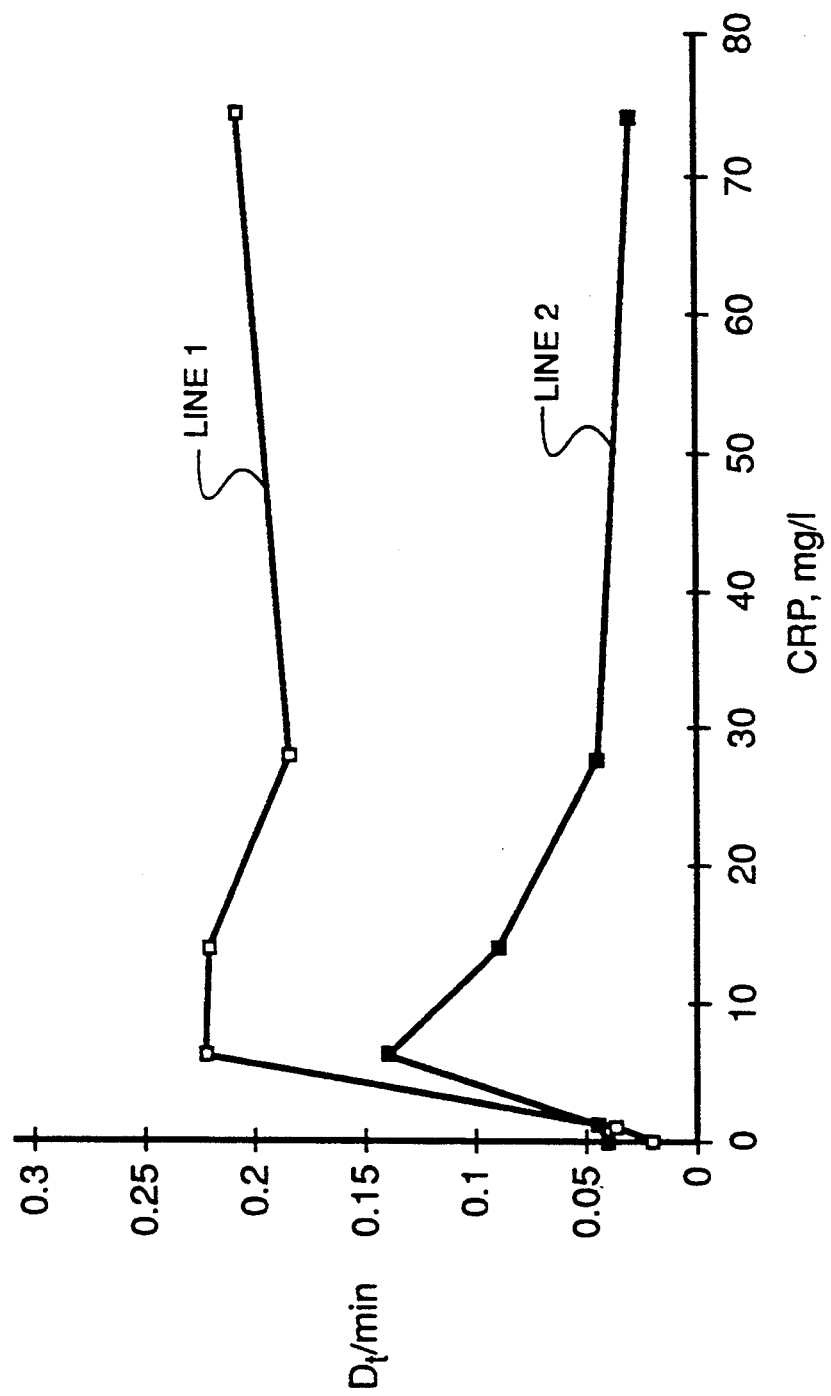

USE OF CALCIUM IN IMMUNOASSAY FOR MEASUREMENT OF C-REACTIVE PROTEIN

FIELD OF THE INVENTION

This invention relates to clinical chemistry. More specifically, this invention relates to a method for the improvement to the measurement of C-Reactive Protein.

BACKGROUND OF THE INVENTION

C-Reactive Protein ("CRP" herein) is normally a trace constituent in blood where the serum concentration in healthy adults normally remains below 5 mg/l. After the onset of a stimulus, such as, tissue injury, inflammation, and various infections, the concentration rapidly and dramatically rises several thousand-fold or more. Upon healing or recovery of the patient and subsequent reduction of the stimulus, the concentration of CRP returns to the trace value. Monitoring disease activity by measuring the concentration level of CRP has become a much used practice in clinical chemistry.

One type of noncompetitive assay particularly useful for the measurement of CRP involves the formation of a "sandwich" of the ligand between two specific binding receptors (and thus is commonly referred to as a sandwich assay). One of the receptors is attached to a water insoluble substrate and the other receptor is commonly labeled with a substance that generates a measurable signal. The two receptors typically recognize two spatially distinct sites on the ligand. Because one of the receptors is attached to the insoluble support, the entire "sandwich" of ligand and two receptors is also insoluble once formed. Consequently, the insoluble "sandwich" may be easily separated from soluble materials (including the unreacted labeled receptor). After separation, either the insoluble "sandwich" may measured (or the unbound labeled receptor may be measured) to indicate the concentration of the ligand.

The receptors in sandwich assays may be various components capable of specifically binding with the targeted C-Reactive Protein. Typically, antibodies specific to CRP as well as modified phosphorycholine (as disclosed in UK Patent Application 2217335A) have been used as receptors in immunoassay systems specific to CRP.

One problem that has been observed in using sandwich assays for the detection of CRP is the potential misinterpretation of results generated by the signal system of the assay. It is particularly difficult to measure (and detect) CRP because of the ligand's widely varying concentration range from trace values to increases of several thousand fold. A "hook" effect has been associated with CRP assays when the CRP is present at high concentrations. As familiar to those skilled in the art, when the CRP is present at high concentrations, the assay may give a false negative result that the CRP is present in low amounts although the CRP concentration is actually very high. The term "hook" describes the calibration curve of the assay having the false negative, where the calibration line resembles a hook. For obvious reasons, reliance on an assay having a "hook" effect is potentially hazardous.

Cragle et al (U.S. Pat. No. 4,595,661 issued Jun. 17, 1986) describe an immunoassay method of reducing the "hook" effect by employing low affinity antibodies in addition to the two receptors typically used.

Although many advances have been made in specific binding assays, it is highly desirable to discover an alternative specific binding sandwich assay system that is capable of improving the measurement of CRP.

SUMMARY OF THE INVENTION

The present invention provides a specific binding immunoassay method comprising:

(1) contacting a liquid sample containing C-reactive protein (CRP) in the presence of calcium ions with (a) a first antibody Ab1 specific for CRP, Ab1 being immobilized on a water-insoluble substrate and (b) a labeled, unbound second antibody Ab2 specific for CRP to obtain a water-insoluble complex of Ab1, CRP, and Ab2;

(2) separating the water-insoluble complex from the liquid sample and unreacted Ab2; and (3) measuring either the amount of Ab2 associated with said water-insoluble complex or the amount of unreacted Ab2 as an indication of the amount of CRP in the sample.

In a second embodiment, a novel analytical element has been discovered for measuring CRP. The analytical element comprises a porous spreading zone and in the porous spreading zone, or a different zone, a first antibody Ab1 specific to CRP, Ab1 being immobilized on a water-insoluble particulate substrate; a labeled, unbound second antibody Ab2 specific for CRP, wherein calcium is incorporated into said porous spreading zone.

Unexpectedly, the presence of calcium ions improves the signal system of a sandwich assay specific to CRP sufficient to avoid the "hook" effect. The CRP may be quantified whether present in the specimen at a very low or a very high concentration without risk of false negative results when CRP is present in high concentrations. Further, the presence of calcium has not been found to interfere with the measurement of CRP when CRP is present in low concentrations in the sample.

BRIEF DESCRIPTION OF DRAWING

The FIGURE is a graph illustrating the quantitative results achieved with the present invention (line 1) as compared with the "hook" effect resulting when a control is employed (line 2).

DETAILED DESCRIPTION OF INVENTION

The invention may be used to assay biological fluids or fluid preparations of human or animal tissue. Biological fluids that may be assayed include, but are not limited to, whole blood, plasma, sera, lymph, bile, urine, spinal fluid, sputum, perspiration and the like, as well as stool secretions. Fluid preparations of human or animal tissue that may be assayed include, for example, skeletal muscle, heart, kidney, lungs, brains, bone marrow, skin and so on. Most preferably, human serum is the fluid to be measured.

Ab1 and Ab2 are the receptors that specifically bind to CRP. As used herein, the receptors have been designated first antibody ("Ab1") and second antibody ("Ab2") for clarification purposes rather than to indicate any kind of direction or mechanism of the assay system. Either Ab1 or Ab2 may be a monoclonal antibody or a polyclonal antibody specific to CRP, as preparable by any known process to those skilled in the art. For example, Ab1 may be a monoclonal antibody while Ab2 may be a polyclonal antibody, or Ab1 may be a polyclonal antibody while Ab2 is a monoclonal antibody. Alternatively, Ab1 and Ab2 may both be polyclonal antibodies (or Ab1 and Ab2 may both be monoclonal antibodies). The antibodies defining Ab1 and Ab2 are those that specifically bind to the targeted CRP, including, whole, fragments, derivatives, and mixtures thereof of the polyclonal antibody.

It is particularly unexpected that when Ab1 is a polyclonal antibody, that the inclusion of calcium ions into the assay improves the results (due to the complexity of the polyclonal antibody molecule). More preferably, Ab1 is defined as a polyclonal antibody and Ab2 is defined either as a monoclonal antibody or polyclonal antibody. Most preferably, Ab1 is defined as a polyclonal antibody and Ab2 is defined as a monoclonal antibody.

To serve as the capture agent, Ab1 is immobilized on a water insoluble substrate. Ab2 represents a labeled antibody. As mentioned previously, although Ab1 and Ab2 may be selected from antibodies that will specifically bind to the targeted ligand, Ab1 and Ab2 represent two different antibodies such that Ab1 and Ab2 specifically bind to two spatially distinct sites on the targeted ligand. Additional antibody entities (such as low affinity antibodies or additional unbound Ab1 or unlabeled Ab2) may also be included in the assay format (either in the fluid sample prior to contacting the element or incorporated into the element) for purposes of assisting in improving the measurement of CRP, as described in U.S. Pat. No. 4,595,661 (issued to Cragle et al. in 1986) and copending U.S. application Ser. No. 07/994,009 filed same day by A. Wu (entitled: "Improvement of The Dynamic Range In Specific Binding Assays").

The water-insoluble substrate that is used to capture Ab1 may be prepared from inorganic and/or organic materials that will maintain their structural integrity when exposed to water or biological fluids. Suitable inorganic materials that may be used in preparing the water-insoluble substrate include siliceous materials {such as, glass (porous glass, frosted glass and so on), silica (silica gel, colloidal silica and so on), bentonite, wollastonite, cordierite, and the like}; and nonsiliceous metal oxides {such as alumina, spinel, apatite, hydroxy apatite, titania, zirconia and magnetic substances (such as iron oxides, ferrite, nickel oxides, cobalt oxides, and the like)}. Suitable organic materials that may be used in preparing the water-insoluble substrate include polymeric particles (such as, for example, polystyrene and derivatives thereof, acrylic polymers, polymethacrylates, polyolefins, halogen-containing polymers, polyesters, and polyamides), polysaccharides, cellulose, dextran, agarose, paper, polypeptide, collagen, and the like.

The water-insoluble substrate may be particulate in nature (varying from a finely divided powder, such as a magnetic ferrofluid, to a coarse granular material) or may be a shaped article, such as beads, test tubes trays, microtiter plate, membrane, film, filter paper, discs, and so on.

Preferably, Ab1 is immobilized on a water-insoluble particulate substrate having a particulate size ranging from about 0.01 $\mu$m to about 20 $\mu$m, more preferably from 0.1 $\mu$m, and most preferably from 0.2 $\mu$m to 1.2 $\mu$m.

Water-insoluble substrates particularly useful in this invention include those particles prepared from polymers having reactive groups which will readily react with Ab1. Examples of such reactive groups include active halogen groups, active ester groups, vinyl groups, aldehyde groups, aziridine groups, epoxy groups, carboxy groups, vinylsulfonyl, activated 2-substituted ethylsulfonyl, and primary amine groups. Useful methods of making polymers incorporating these reactive groups and methods for reacting these polymers with materials such as Ab1 are well-known and described, for example, in U.S. Ser. No. 315,086 (filed Feb. 24, 1989, corresponding EPA 0 323 692); U.S. Ser. No. 646,132, U.S. Pat. No. 5,200,462 (filed Jan. 25, 1991, corresponding EPA 0 496 472); U.S. Ser. No. 646,303, U.S. Pat. No. 5,308,749 (filed Jan. 25, 1991, corresponding EPA 0 496 472); U.S. Ser. No. 539,768, abandoned (filed Jun. 18, 1990, corresponding EPA 0 466 220); U.S. Ser. No. 373,304, (filed Jun. 29, 1989, corresponding EPA 0 308 235); U.S. Ser. No. 539,680, U.S. Pat. No. 5,155,166 (filed Jun. 18, 1990, corresponding EPA 0 426 670); and U.S. Ser. No. 389,390, U.S. Pat. No. 5,266,500 (filed Aug. 3, 1989, corresponding EPA 0 411 711). Also employable as insoluble substrates are core/-shell polymers, as described in U.S. Pat. No. 4,997,772, and polymer particles that can be dyed, as described in U.S. Pat. No. 5,053,443 (issued Oct. 1, 1991) and in U.S. Ser No. 612,364, abandoned (filed Nov. 14, 1990, corresponding EPA 0 308 233), U.S. Pat. No. 5,147,777 (issued Sep. 15, 1992); U.S. Pat. No. 5,149,737 (issued Sep. 22, 1992); U.S. Ser. No. 856,279, U.S. Pat. No. 5,210,289 (filed Feb. 23, 1992); and U.S. Ser. No. 876,672, U.S. Pat. No. 5,262,297 (filed Apr. 30, 1992).

Among the water-insoluble substrates more preferred for the immobilization of Ab1 are particles prepared of polymers containing activated 2-substituted ethylsulfonyl groups, particularly 2-halo ethylsulfonyl groups, or polymers containing reactive carboxy groups.

Ab1 may be immobilized onto the water-insoluble substrate by any means known those skilled in the art, including, for example, chemical coupling, simple adsorption, or employing specific binding pairs, as known in the art. For example, chemical coupling can involve treating the insoluble substrate with one or more chemical compounds (silanes, polyisocyanates and the like), followed by contacting the treated water-insoluble substrate with an aqueous solution of Ab1. Alternatively, the substrate may have reactive groups for covalent coupling with Ab1. As known in the art, for example, adsorption can be accomplished by contacting an aqueous solution of Ab1 with the insoluble substrate for a time sufficient to permit the desired or maximum degree of immobilization. As described in U.S. Ser. No. 136,165, abandoned filed Jan. 18, 1987, corresponding to EPA 0 302 715, specific binding pairs such as avidin an biotin, a lectin, and a sugar may also be employed.

Most preferably, when Ab1 represents an antibody, the water-insoluble substrate is poly[styrene-co-m and p-(2-chloroethylsulfonylmethyl)styrene] bead covalently bound to Ab1 with techniques such as, for example, that described in EPA 0 323 692.

According to the invention, Ab2 is labeled with one or more suitable substances that is capable of generating a measurable signal either alone, or in conjunction with other reactants, as is known to those skilled in the art. Suitable substances that may be attached to Ab2 as a label include, but are not limited to, one or more of the following: radioactive isotopes (such as $I^{125}$ and the like), enzymes (such as, betagalactosidase, alkaline phosphatase, glucose oxidase and horseradish peroxidase, and the like), fluorescent substances (such as, europium, europium derivatives, and the like), chemiluminescent substances (such as, for example, luminol derivatives), dyes (such as, for example, leuco dyes and fluorescent dyes), and so on. Preferred labels are enzymatic labels such as alkaline phosphatase, glucose oxidase, and horseradish peroxidase (HRP). The most preferred label for Ab2 is HRP.

Any number of techniques known to those skilled in the art may be employed in attaching the labeling substances to Ab2. Preferably, the labeling substance is covalently bound to Ab2 with any suitable technique.

When Ab2 is labeled with an enzymatic substance, other reactants (typically a substrate for the enzyme) are included in the assay system. When the inventive assay is prepared as such, the substrate for the enzyme may be included in the assay system prior to the introduction of the liquid sample, simultaneously with the liquid sample or after completion of the binding reaction of the sandwich, as known to those skilled in the art. The enzymatic substrate may be a material which is directly acted upon by the enzyme label, or a material that is involved in a series of reactions which involve enzymatic reaction of the label. For example, if the enzyme label is a HRP, the substrate may be hydrogen peroxide. If the enzyme is glucose oxidase, the substrate is glucose.

Additionally, when enzymatic labels are used, an indicator composition may be employed in the assay system comprising one or more reagents which provide a detectable species as a result of reaction of the label. Preferably, the indicator composition is a colorimetric indicator which provides a colorimetrically detectable species as a result of enzymatic reaction with the substrate. The indicator composition may be a single compound or combination of reagents which produce a detectable dye or chemiluminescent emission of light upon the enzymatic reaction, as known in the art and described in U.S. Pat. Nos. 4,729,950 and 4,598,044 (both issued to Kricka et al.). For example, when glucose oxidase is used as the enzyme label, glucose may be used as the substrate to form gluconic acid upon a reaction, whereupon a colorimetric indicator composition may be employed that has a coupler and oxidizable compound which react with the gluconic acid to produce a dye. Alternatively, when HRP (or another suitable peroxidative compound) is used as the enzyme label, then a leuco dye which generates a detectable dye in the presence of peroxidase and hydrogen peroxide may be employed. Suitable leuco dyes include, but are not limited to those described in U.S. Pat. No. 4,089,747 (issued May 16, 1978, to Bruschi); U.S. Pat. No. 4,670,385 (issued Jun. 2, 1987, to Babb et al.); and U.S. Pat. No. 4,828,983 (issued May 9, 1989, to McClune). A most preferred leuco dye is a triarylimidazole leuco dye.

When leuco dyes are employed, preferably the dye(s) are dissolved into an organic solvent. Most preferably, the organic solvent employed is sodium dodecyl sulfate (SDS). The entire solvent-dye emulsion may be incorporated into the element.

According to the invention, the calcium ions are present in the assay in an amount sufficient to reduce the "hook" effect of the signal system. The method of this invention is adaptable to both solution assays as well as dry analytical elements. Preferably, calcium ions are present in an amount ranging from about 0.01M to about 0.5M, more preferably 0.02M to 0.2M, and most preferably about 0.1M (as present in the assay solution or in the dry coating coverage when incorporated into the dry analytic element). Any suitable form of the calcium ions may be employed such as, calcium chloride, calcium acetate, calcium bromide, calcium iodide, calcium nitrate, and so on, (preferably in solution), as widely commercially available. Most preferably employed because of cost and availability is $CaCl_2.H_2O$. The calcium ions may be incorporated into the assay system in the sample fluid prior to contact with the assay, or incorporated into the assay such that contact is made between the calcium and fluid sample prior to or during the immuno reaction of Ab1-CRP-Ab2.

When the immunoassay is prepared as a solution assay, the analytical compositions (and indicator composition, if included) is contacted with the liquid sample containing the CRP in a suitable container (for example, test tube, petri dish, beaker, cuvette, and so on).

When the method of the invention is practiced with a dry analytical element, dry analytical element formats especially useful in the practice of this invention are those having a porous spreading zone (prepared from porous particulate structures, porous polymeric films, porous reflective polymer beads, cellulose, glass fibers, woven and nonwoven fabrics, and the like) and a non-porous, transparent support (prepared from paper, metal foils, polystyrene, polyesters, polycarbonate, cellulose esters, gelatin, and so on). It is desirable that the spreading layer be isotropically porous, having the same porosity in each direction of the zone. Such spreading zones are prepared from a number of materials including a structure of adhered particles as described, for example, in U.S. Pat. No. 4,258,001 (Pierce et al) and pigmented zones such as those described in U.S. Pat. No. 3,992,158 (Przybylowicz et al). Interconnection of the particles comprising the bead spreading zone may be interconnected spaces or pores between particles, fibers, polymeric strands, and so on.

Preferred spreading zones are those described in U.S. Pat. No. 3,992,158 as "blush polymer" zones. Such zones can be formed on a supporting material by dissolving a polymer in a mixture of two organic liquids, one of which is a lower boiling, good solvent for the polymer and other being a high boiling, non-solvent or poor solvent for the polymer. The resulting polymer solution is coated on the supporting material and dried under controlled conditions to leave an isotopically porous zone. Various polymers are known to be useful in this context including, but not limited to, polycarbonates, polyamides, polyurethanes and cellulose esters such as cellulose acetate (which is preferred).

Optionally within the porous zone may be incorporated particulate materials of various sizes to enhance the void volume. Useful particulate materials include, but are not limited to, inorganic pigments such as titanium dioxide, barium sulfate, zinc oxide, lead oxide with titanium dioxide being preferred. Further details of the preparation of "blush polymers" are described in U.S. Pat. No. 3,992,158.

Preferably, the porous spreading zone is the outermost zone of the element (if more than one zone is used). The porous spreading zone prepared from any of the known materials used for such zones as described, for example in U.S. Pat. No. 4,292,272 (Kitajima et al), U.S. Pat. No. 3,992,158 (noted above), U.S. Pat. No. 4,258,001 (noted above) U.S. Pat. No. 4,430,436 (Koyama et al) and related U.S. patents, and JP 57(1982)-101760 (published Jun. 24, 1982). Preferably the particulate matter of the porous spreading zone is present in a coverage from about 20 to about 150 $g/m^2$ and more preferably from about 50 to about 150 $g/m^2$.

The dry element of this invention may be divided into two or more contiguous zones (or layers) which are fluid permeable. The zones can be "self-supporting", which means that the zones can be composed of materials which maintain their integrity when exposed to aqueous fluids, such as filter papers or microporous membranes. Preferably, however, such zones are disposed on a separate, nonporous support which is dimensionally stable, inert to chemical reaction and preferably transparent (that is, radiation transmissive for wavelengths between about 200 and 900 nm). However, non-transparent supports can be used if the mode of detection is reflectance spectroscopy instead of transmission spectroscopy. Useful supports are well known in the art, including but not limited to polyesters, papers, metal foils, polystyrene, polycarbonates, and cellulose esters.

The preferred dry analytical elements may contain at least one other zone which contains one or more reagents needed for the assay. Such a zone is often known in the art as a reagent or registration zone, but it can also include a second porous spreading zone if desired or printed layers located on other zones. When more than one porous zone is employed, the calcium is incorporated in at least one of the porous zone (more preferably within the outermost porous zone). The zones are generally in fluid contact with each other, meaning that fluids, reagents and reagent products can pass or be transported between superposed regions of adjacent zones, unless of course, a reagent is immobilized in some manner so it will not migrate within or without a zone. Preferably, the zones are separately coated and superposed layers on an inert support (see Example 1 below). The reagent zones or layers can be composed of one or more binder materials (such as gelatin and other colloidal materials, hydrophilic polymers such as polyvinyl alcohol, polyacrylamide and others known in the art) in which reagents are incorporated.

The methods of preparing such elements are well known in the art and involve application of wet formulations of the zone composition onto a support and drying under suitable conditions. Coating procedures are well described in the art cited above for describing the spreading zones.

The reagents may incorporated in the element in, for example, the same bead spreading layer or separate layer(s), or a combination thereof. Most preferably, the calcium in incorporated into the bead spreading layer. Additionally, when leuco dry solution (preferably dissolved in sodium dodecyl sulfate) is employed, this solution is incorporated into the element as an emulsion (preferably into a reagent layer separate from the spreading layer, more preferably into a gelatin reagent layer).

Although Ab1 and Ab2 may be placed in different or the same zone(s) within the element, a particularly preferred dry analytical element comprises a porous, polymeric bead spreading zone wherein Ab1 is incorporated into the zone. As incorporated, Ab1 is immobilized on a water insoluble particulate substrate dispersed within the spreading zone, with said particulate substrate of the size (as previously described) falling with the range from about 0.001 $\mu$m to 20 $\mu$m. Preferably, both Ab1 and Ab2 are incorporated in the element in the porous spreading zone. Alternatively, Ab1 and Ab2 may both (or separately) be present in solution and not incorporated into the element (with contacting with element occurring before, during or after the fluid sample is contacted with the element).

As known to those skilled in the art, the specimen fluid sample may be physically contacted with the assay system by many methods, for example, using an amount of fluid sample from about 1 $\mu$l to about 200 $\mu$l. After contact, the sample and reagents within the element become mixed within the various zones when more than one zone is employed. Such contact can be accomplished in any suitable manner, for example by dipping or immersing the element into the sample, or preferably, by spotting the sample onto the element by hand or suitable machine.

To obtain the immuno reaction product, a water-insoluble complex of Ab1-CRP-Ab2 (hereinafter "water-insoluble complex"), after the specimen is introduced to the assay system, the assay may be carried out under usual conditions, as known to those skilled in the art. For example, after sample introduction, the element may be exposed to any conditioning, such as incubation, heating, or otherwise, that may be desirable to quicken or otherwise facilitate obtaining a test result. Preferably, assay may be incubated within a temperature range of from 5°–50° C. (preferably 34°–40° C.) for a period of a few seconds to 24 hours. Although the assay may be accomplished over a wide pH range, typically the assay may be carried out within the pH range from about 5 to about 9.

The concentration of the ligand may be measured by quantifying the portion of Ab2 present in the water insoluble complex or the unreacted Ab2 which is left unbound and soluble.

Physical separation of the water insoluble complex from the fluid sample and the unreacted Ab2 may be accomplished with any suitable technique as known to those skilled in the art. For example, after the reaction period, the excess unbound Ab2 may be removed from the water insoluble complex by a washing step by any suitable technique, as known to those skilled in the art.

When utilizing the washing step, the wash fluid employed may be any suitable solution, as known to those skilled in the art. For example, a preferred wash fluid includes distilled water, physiologic saline, phosphate buffer (such as for example $Na_3PO_4$), and the like. More preferably, when the label is an enzyme, the wash solution may also include, for example, a substrate specific for the enzyme, a surfactant [preferably a nonionic surfactant such as, for example, poly(oxyalkylene alcohols)], an electron transfer agent to assist in the oxidation of substrate (including, for example, p,p'-biphenol, p-methoxyphenol, o-methoxyphenol, p-anisidine, p-hydroxy-N,N'-dimethylaniline, or o-phenylenediamine, and 4'-hydroxyacetanilide), and a complexing agent [such as, for example, acid derivatives including acetic acid derivatives of di-, tri-, and tetra-amino compounds (such as ethylenediamine tetraacetic acid and diethylenetriamine pentaacetic acid)]. Particularly effective as a wash fluid when the label is a horseradish peroxidase and the colorimetric indicator is a leuco dye, is a phosphate buffered solution of hydrogen peroxide (the substrate) with an electron transfer agent (most preferably 4'-hydroxyacetanilide) to assist in oxidation of the hydrogen peroxide, and a complexing agent (most preferably diethylenetriamine pentaacetic acid). Other assay formats may also be used, such as, for example, those described in U.S. Ser. No. 539,774 U.S. Pat. No. 5,147,777 (corresponding EPA 0 462 644).

Detection of Ab2 for purposes of measuring the concentration of the CRP may be accomplished by methods known to those skilled in the art, including, for example, measuring the signal of the immunoassay through radioimmunoassay, enzyme immunoassay, fluorescence immunoassay, chemiluminescence immunoassay, and the like. Although the inventive assay is especially well-suited for quantitative analysis, the assay is equally well suited for qualitative analysis.

The present invention is now further illustrated by, but is by no means is limited to, the following examples.

EXAMPLES

In each of the examples, the assays employed a dry analytical element and wash solution. The leuco dye was the triarylimidazole leuco blue color dye 4,5-Bis(4-dimethylaminophenyl)-2-(4-hydroxy-3,5-dimethoxyphenyl)imidazole. As noted in the elements, q.s. indicates the amount of deionized, distilled water needed to fulfill the total wet coverage for each layer described. Other materials used for the element and wash solution were obtained as follows: SURFACTANT 10G (a isononylphenoxypolyglycidol surfactant) supplied by Olin Corporation (Stamford, Conn., U.S.A.), TRITON™ X-100 nonionic surfactant supplied by Rohm and Haas (Philadelphia, Pa., U.S.A.), ZONYL™ FSN nonionic surfactant supplied by DuPont (Wilmington, Del., U.S.A.), horseradish peroxidase supplied by Sigma Chemical Co. (St. Louis, Mo., U.S.A) or Miles Laboratories (Elkhart, Ind., U.S.A.), and the remainder of the components described below in the film element or wash solution supplied by either Eastman Kodak Company (Rochester, N.Y., U.S.A.) or are preparable using standard procedures and readily available starting materials, as known to those skilled in the art.

| ELEMENT A | | |
|---|---|---|
| LAYER | COMPONENT | COVERAGE (g/m$^2$) |
| 02 BEAD SPREADING LAYER | TOTAL WET COVERAGE | 270 |
| | Deionized distilled water | q.s. |
| | N-[Tris(hydroxymethyl)methyl]-2-aminoethanesulfonic acid buffer (pH 7.55) | 0.219 |
| | 5,5-Dimethyl-1,3-cyclohexanedione | 0.5 |
| | Poly (methyl acrylate-co-sodium 2-acrylamido-2-methylpropanesulfonate-co-2-acetoacetoxyethyl methacylate) | 2.583 |
| | Poly(m- and p-vinyltoluene-co-methacrylic acid) particles having a an average diameter of 30 μm | 130.0 |
| | CaCl$_2$.H$_2$O | 1.4 |
| | ZONYL FSN | 0.054 |
| | Methanol | 0.675 |
| | Bovine serum albumin | 0.5 |
| | Particles of poly[styrene-co-m-& p-(2-chloroethylsulfonylmethyl) styrene] covalently bound to CRP polyclonal antibody (Ab1) | 0.16 |
| | Monoclonal antibody | 0.01 |
| | Monoclonal antibody-HRP (Ab2) | 0.001 |
| | 4'-Hydroxyacetanilide | 0.15 |
| 01 GEL | TOTAL WET COVERAGE | 139 |
| | Distilled deionized water | q.s. |
| | Bone gelatin | 5.00 |
| | 4'-hydroxyacetanilide | 0.15 |
| | N-[Tris(hydroxymethyl)methyl-2-aminoethanesulfonic acid buffer (pH = 7.0) | 4.58 |
| | 4,5-Bis(4-dimethylaminophenyl) 2-(4-hydroxy-3,5-dimethoxyphenyl) imidazole leuco dye | 0.15 |

-continued

| ELEMENT A | | |
|---|---|---|
| | sodium dodecyl sulfate | 1.34 |
| | TRITON X-100 | 0.004 |
| | Bis(vinylsulfonylmethyl) ether | 0.15 |
| SUPPORT | Poly(ethylene terephthalate) | |

| WASH FLUID FORMULA | |
|---|---|
| Hydrogen Peroxide | 0.03% |
| Sodium Phosphate, pH 6.8 | 0.01 M |
| 4'-Hydroxyacetanilide | 0.005 M |
| Diethylenetriaminepentaacetic acid | 10 μM |
| Distilled deionized water | q.s. |

EXAMPLE 1

The first layer of the element (layer 01) was coated on subbed, Gel-washed poly(ethylene terephthalate) support, with the second layer (layer 02) was coated on top.

Ab1 was a polyclonal anti-CRP goat antibody (purchased from DiaMed Company, South Windham, Me., U.S.A.) that was covalently bonded to polymeric bead particles of poly[styrene-co-m &-p-(2-chloroethylsulfonylmethyl)styrene], as described in U.S. Ser. No. 315,086 (corresponding EPA 0 302 715 B1) and U.S. Ser. No. 742,198, U.S. Pat. No. 5,177,023 with a weight ratio of 90/10; size 0.42 μm. The calcium was coated on the bead spreading layer in an amount of 1.4 g/m$^2$ (0.1M).

Fluid samples of the antigen CRP (purchased from Scripps Laboratories) were prepared in concentrations varying from no CRP (the control) to 25.6 mg/l of CRP (as shown in TABLE I hereinafter) in a diluent of 1% mouse serum in solution of sodium phosphate (0.01M having a pH of 6.8) and sodium chloride (0.15N). The monoclonal antibody [added in excess unlabeled as well at attached to horseradish perioxidase (HRP) to form Ab2] was purchased from Medix Biochemica, Finland. The horseradish perioxidase label attached to the monoclonal antibody was accomplished by a thiol/maleimide procedure, as described in *Clinical Chemistry*, vol. 30, pp. 1446–1451 (1984). Ten μl of the CRP serum solution was spotted on a film element for each concentration of CRP. The spotted elements were then incubated at 37° C. for 5 minutes. Thereafter 10 μl of the wash solution was applied to the element at a position that was 2.8 mm away from the center point at which the sample was applied to the element. The excess HRP conjugated antibody (Ab2) was removed from the observation area which was at the center of the element. The wash also operated to initiate the HRP-catalyzed dye oxidation.

The elements were then placed back in the incubator at 37° C. The amount of immuno complex of Ab1-CRP-Ab2 sandwich was determined by measuring the rate of the triarylimidazole leuco dye oxidation by hydrogen peroxide in the center of the element in about a 0 to 1 minute read time window.

The rate of increase of the transmission density ($D_t$/min) of each washed element was measured by a reflectometer as described in *J. Optical Soc. Am.*, 43, 595 (1953). Data are recorded in TABLE I below with calibration curve of the data shown in the FIGURE as line 1. As shown, a substantial improvement in the signal system was observed.

Comparative Example 1

Fluid samples of CRP were prepared in the concentrations as described in Example 1. This example demonstrates a comparison, where the same element was employed, only omitting the calcium in the element formation.

A total of 10 μl of the CRP and Ab2 solution was spotted on the film element for each concentration of CRP. The spotted elements were then incubated, washed, and measured as described in Example 1. The data are recorded in TABLE I, hereinafter, with calibration curve of the data shown in the FIGURE as line 2. As the comparative calibration curve indicates, in the absence of calcium, the "hook" effect starts at approximately 10 mg/l CRP. In the presence of calcium, however, no "hook" effect was observed in the concentration levels tested.

TABLE I (Example 1 and Comparative Example 1)

| CRP (mg/l) | Lines | |
|---|---|---|
| | 1 Signal ($D_r$/minute) | 2 |
| 0 | 0.01705 | 0.0384 |
| 1.0 | 0.03422 | 0.04288 |
| 6.0 | 0.22210 | 0.13889 |
| 14.0 | 0.22072 | 0.08703 |
| 28.0 | 0.18452 | 0.04310 |
| 74.0 | 0.20851 | 0.03015 |

Lines (as correspond to Fig.)
1. With presence of $CaCl_2$ in element –Example 1
2. Without presence of $CaCl_2$ in element – Comparative Example 1

The data shown in TABLE I illustrate the measurement of CRP. The unexpected advantage of employing calcium in the element is shown in the FIGURE.

The invention has been described above with particular reference to preferred embodiments. A skilled practitioner familiar with the above detailed description may make many modifications and substitutions without departing from the scope and spirit of the invention. Articles, patent applications, and issued patents cited herein are hereby incorporated by reference.

That which is claimed is;

1. A specific binding assay method comprising:
   (1) contacting a liquid sample containing C-reactive protein (CRP) in the presence of from 0.01M to 0.5M calcium ions with (a) a first polyclonal antibody Ab1 specific for CRP, Ab1 being immobilized on a water-insoluble substrate and (b) a labeled, unbound second monoclonal antibody Ab2 specific for CRP to obtain a water-insoluble complex of Ab1, ligand, and Ab2;
   (2) separating the water-insoluble complex from the liquid sample and unreacted Ab2; and
   (3) measuring either the amount of Ab2 associated with said water-insoluble complex or the amount of unreacted Ab2 as an indication of the amount of C-reactive protein in the sample.

2. A method according to claim 1 wherein said calcium is present in an amount ranging from 0.02M to 0.2M.

3. A method according to claim 1 wherein said calcium is present in an amount of about 0.1M.

4. A method according to claim 1 wherein said calcium is incorporate into said fluid sample prior to said contacting in step (1).

5. A method according to claim 1 wherein said label on Ab2 is an enzyme.

6. An analytical element comprising a porous spreading zone and in the porous spreading zone, or a different zone, a first polyclonal antibody Ab1 specific to C-Reactive Protein (CRP), Ab1 being immobilized on a water-insoluble particulate substrate and a labeled, unbound second monoclonal antibody Ab2 specific for CRP, wherein calcium ions are incorporated into said porous spreading zone in an amount ranging from 0.01M to 0.5M.

7. A method according to claim 6 wherein said calcium is present in an amount ranging from 0.02M to 0.2M.

8. A method according to claim 7 wherein said calcium is present in an amount of about 0.1M.

* * * * *